United States Patent [19]

Owen

[11] Patent Number: 4,694,507

[45] Date of Patent: Sep. 22, 1987

[54] WELDER'S HOOD HAVING A CHIN OPERATED WINDOW CLOSURE

[76] Inventor: Steven M. Owen, R.R. 1, Box 136, Henry, S. Dak. 57243

[21] Appl. No.: 905,548

[22] Filed: Sep. 10, 1986

[51] Int. Cl.$^4$ ............................................... A61F 9/06
[52] U.S. Cl. ................................................... 2/8; 2/9
[58] Field of Search ........................... 2/8, 9, 427, 432

[56] References Cited

U.S. PATENT DOCUMENTS

| | | | |
|---|---|---|---|
| 2,896,215 | 7/1959 | Fernandez | 2/8 |
| 3,086,213 | 4/1963 | Crozat et al. | 2/8 |
| 3,339,207 | 9/1967 | Perry | 2/8 |
| 3,490,071 | 1/1970 | Marshall | 2/8 |
| 3,517,392 | 6/1970 | Hodge et al. | 2/8 |
| 3,775,774 | 12/1973 | Herman | 2/8 |
| 4,539,713 | 9/1985 | Hodge | 2/8 |

Primary Examiner—Werner H. Schroeder
Assistant Examiner—Judith L. Olds
Attorney, Agent, or Firm—James E. Staudt

[57] ABSTRACT

A mechanism for opening and closing a window closure member (12) in a welder's helmut (10) by movement of the welder's chin. The helmet is provided with a chin engaging member (18), (20) which is attached to one end of an arm (24) by a rod (26). The arm (24) is pivotally connected to the helmut. As the welder lowers his chin against the chin engaging member, a roller (30) attached to the other end of pivoting arm (24) applies an opening force via rod (26) to the lower inner face of the window closure member (12) thus forcing the closure member to swing open about hinges (14). The chin engaging member is biased against the welder's chin by a spring (40). Thus an upward movement of the welder's chin will allow the window closure member (12) to return to a closed position.

6 Claims, 8 Drawing Figures

1

WELDER'S HOOD HAVING A CHIN OPERATED WINDOW CLOSURE

BACKGROUND OF THE INVENTION

Welder's hoods typically are provided with a sight opening in line with the wearer's eyes. A window closure member is hinged to the hood for movement between open and closed positions. Colored glass is secured in the closure member to protect the wearer's eyes from arcs generated during the welding operation. Typically the glass is darkly colored and prevents the wearer from being able to see through the glass except during the welding operation. For the welder to see while wearing the hood it is necessary to move the closure member out of his line of sight. This is accomplished by pivoting the eye closure member by hand. However, movement of the hand and arm to operate the closure member tends to cause the welder to also move the hand and arm in which he holds the welding equipment. Such movement makes it quite difficult to strike the initial arc in the desired location.

It is therefor an object of the present invention to provide a mechanism for movement of the colored glass to and from the line of sight of a welder without use of the welder's hands.

It is another object of the present invention to provide a welding hood with a mechanism for opening and closing the window closure member by movement of the welder's chin, thereby permitting the welder full use of both hands at all times.

A further object of the present invention is to provide a mechanism for a chin actuated window closure which is adaptable for use on most existing welding hoods.

SUMMARY OF THE INVENTION

The invention is a mechanism for movement of a window closure member from the line of sight of a welder. The mechanism is operated by the chin of the welder and includes a chin engaging member pivotally secured to a welders hood. An actuator rod is secured at one end thereof to the chin engaging member and at its distal end is secured to a pivotally mounted closure member engaging assembly. This assembly engages the closure member for upward pivotal movement thereof, whereby the welder may see through the window in the hood without having his sight obscured by the colored glass. The engaging assembly includes an arm pivotally secured to the hood adjacent the window. The distal end of the actuator rod is secured to one end of the arm and a roller is secured to the other end of the arm. The roller engages the window closure in response to pivotal movement of the arm in response to movement of the chin engaging member.

DETAILED DESCRIPTION OF THE INVENTION

Figure 1:
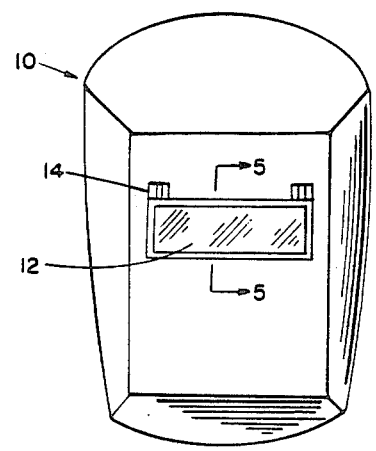
FIG. 1 is a front elevational view of a welder's mask.
Figure 2:
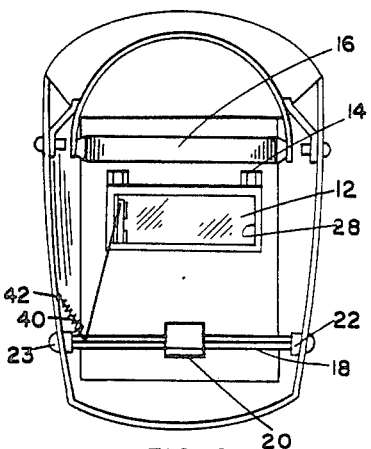
FIG. 2 is a rear elevational view of the mask of FIG. 1.
Figure 3:
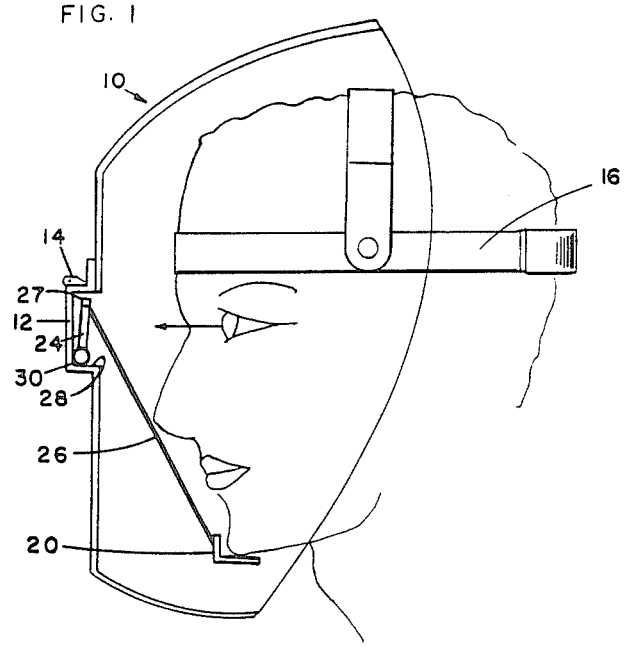
FIG. 3 is a side elevational view showing in phantom the mask being fitted to a person's head.
Figure 4:
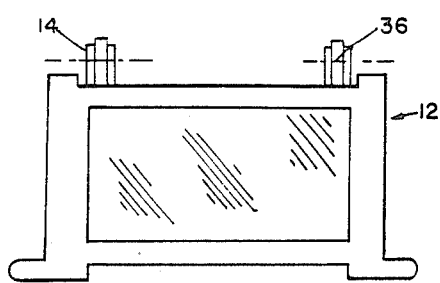
FIG. 4 is an enlarged view of the window of the mask of FIG. 1.

As seen in FIG. 1 a welding hood 10 includes a window closure member 12 pivotally secured thereto by hinges 14. FIG. 2 is a rear view of the hood illustrating a strap 16 for retaining the hood on a welder's head. The mechanism for pivoting closure member 12 between open and closed positions includes a chin engaging member 18 which is provided with an arcuate configuration having a chin rest 20 thereon. Chin engaging member 18 is pivotally and adjustably secured to the hood at its ends 22 and 23 (FIG. 2).

Figure 5:
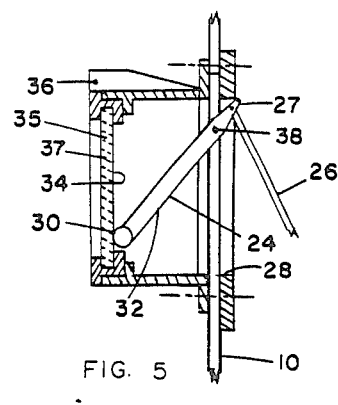
FIG. 5 is a partially sectional view along line 5—5 of FIG. 1.
Figure 6:
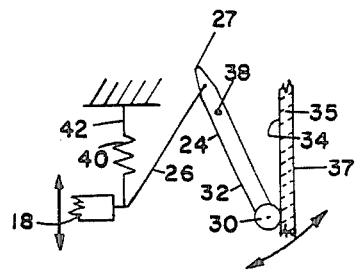
FIG. 6 is a diagrammatic illustration of the opening and closing mechanism of the present invention.

To impart pivotal movement to closure member 12, a rod 26 is secured to the chin engaging member 18 and extends upwardly for pivotal connection to the upper end 27 of an arm 24 which in turn is pivotally secured to the hood adjacent a window opening 28. As best illustrated in FIG. 5 the closure member 12 includes a glass 35 having an inner surface 34 and an outer surface 37. A roller 30 (FIG. 5) is secured at the lower end 32 of arm 24 for engagement with the inner surface 34 of glass 35 carried in closure member 12. A pin 38 disposed between the upper end 27 and lower end 32 of arm 24 secures arm 24 to the hood. For most effective use, the distance from pin 38 to the center of roller 30 must be 4 to 7 times the distance from pin 38 to pivot point of the rod 26 in the arm 24. A spring 40 biases the chin engaging member 18 upwardly in response to the release of pressure by the welder's chin.

Figure 7:
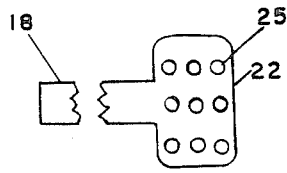
FIG. 7 is an enlarged view of one end of a chin engaging member.

To accommodate different size welders it will be noted in FIG. 7 that the end portions 22, 24 of the chin engaging member 18 are provided with a series of vertically and horizontally aligned holes 25. These holes provide an adjustment for the attachment of the chin engaging member 18 to the hood 10.

Figure 8:
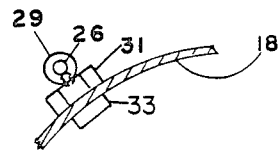
FIG. 8 is an enlarged view of a fastener for attaching the actuator rod of the invention to the chin engaging member.

As illustrated in FIG. 8 the rod 26 is attached to the chin engaging member 18 by a multiple function fastener consisting of a hollow cylinder 29, a spacer 31 and a screw 33. The screw passes through the chin engaging member 18, through the spacer 31, threadedly engages cylinder 29 and firmly abuts rod 26. This arrangement provides a fastener for connection of rod 26 to member 18 which permits adjustment of the rod length by sliding rod 26 to the desired position within cylinder 29. It will also be noted that the bolt 33 when provided in a proper length will provide a firm but pivital connection of the fastener to the engaging member 18, thus avoiding any binding in the rod or its connection.

From the foregoing it will be seen that an improved welder's hood has been devised which permits the movement of the protective colored glass from the welder's line of sight without use of the welder's hands, thus leaving the welder's hands free to hold the welding equipment and if necessary a part of the material to be welded. This improvement is provided with a mechanism which is operated by the welder's chin and which utilizes a unique design which is not only more simple and economical than other known devices, but is particularly well suited for use on conventional welder's hoods now in use.

While the invention has been shown in but one form, it will be obvious to those skilled in the art that it is not so limited but is susceptible to various other changes and modifications without departing from the spirit thereof.

I claim:

1. In a hood having an opening therein and a closure member having inner and outer surfaces, said closure member being pivotally secured to said hood over said opening, a chin operated mechanism for opening and closing said opening comprising;
   a. a chin engaging member pivotally mounted in said hood for pivotal movement between first and second positions;
   b. an arm pivotally secured to said hood adjacent said opening;
   c. a rod having one end pivotally secured to said chin engaging member and a second end pivotally secured to a first end of said arm;
   d. a roller pivotally secured to a second end of said arm, said roller being disposed in engagement with the inner surface of said closure member, said closure member disposed for pivotal movement to an open position responsive to movement of said roller thereacross in response to pivotal movement of said arm responsive to downward movement of said chin engaging member to said second position; and,
   e. a spring secured to said hood and to said chin engaging member for biasing said chin engaging member toward said first position.

2. The mechanism set forth in claim 1 wherein the chin engaging member, the arm, the rod, the roller, and the spring are adapted to be located within said hood.

3. The mechanism set forth in claim 2 wherein said chin engaging member is generally arcuate in shape.

4. The mechanism set forth in claim 3 wherein said chin engaging member includes a series of generally vertically and horizontally aligned holes on each end thereof for selective use in mounting said member to said hood.

5. The mechanism as set forth in claim 1 wherein said rod is attached to said chin engaging member by means of a cylindrical fastener having a longitudinal hole therethrough for slidable reception of said rod and a lateral threaded hole for reception of a bolt which is adapted to pass through said chin engaging member and to abut said rod so as to lock said rod within said cylidner.

6. The mechanism as set forth in claim 1 wherein the distance from the point attachment of said arm to said hood to the point of connection of said roller to said arm is 4 to 7 times the distance from said point of attachment to the point of connection of said arm to said rod.

* * * * *